(12) United States Patent
Leroux et al.

(10) Patent No.: US 11,376,218 B2
(45) Date of Patent: Jul. 5, 2022

(54) METHOD FOR PREPARING TRANSMEMBRANE PH-GRADIENT VESICLES

(71) Applicant: Versantis AG, Zurich (CH)

(72) Inventors: Jean-Christophe Leroux, Zurich (CH); Vincent Forster, Zurich (CH); Valentina Agostoni, Zurich (CH)

(73) Assignee: Versantis AG, Zurich (CH)

( * ) Notice: Subject to any disclaimer, the term of this patent is extended or adjusted under 35 U.S.C. 154(b) by 0 days.

(21) Appl. No.: 15/567,878

(22) PCT Filed: May 3, 2016

(86) PCT No.: PCT/EP2016/059912
§ 371 (c)(1),
(2) Date: Oct. 19, 2017

(87) PCT Pub. No.: WO2016/177741
PCT Pub. Date: Nov. 10, 2016

(65) Prior Publication Data
US 2018/0104189 A1    Apr. 19, 2018

(30) Foreign Application Priority Data

May 4, 2015 (EP) .................................... 15166247

(51) Int. Cl.
*A61K 9/127* (2006.01)
(52) U.S. Cl.
CPC ............ *A61K 9/1277* (2013.01); *A61K 9/127* (2013.01)
(58) Field of Classification Search
CPC .... A61K 9/127; A61K 9/1277; A61K 9/1273; A61K 9/1278; A61K 47/00; A61P 39/02
See application file for complete search history.

(56) References Cited

U.S. PATENT DOCUMENTS

| 4,508,703 A | 4/1985 | Redziniak et al. |
| 4,532,089 A | 7/1985 | MacDonald |

(Continued)

FOREIGN PATENT DOCUMENTS

| AU | 2008203032 A1 | 7/2008 |
| CN | 102626390 B | 5/2013 |

(Continued)

OTHER PUBLICATIONS

Bertrand et al.; "Supplementary information"; ACS Nano; 2010; pp. 1-16.

(Continued)

*Primary Examiner* — Gollamudi S Kishore
(74) *Attorney, Agent, or Firm* — The Webb Law Firm

(57) ABSTRACT

The invention relates to a method for preparing transmembrane pH-gradient vesicles. This method includes the following steps: a) preparing vesicles made from at least one matrix substance in an aqueous medium having an osmolarity of not more than 200 mOsm/l. The matrix substance is chosen from the group consisting of amphiphilic lipids and amphiphilic block copolymers, b) transferring the vesicles into a basic or acidic buffer having an osmolarity being at least 200 mOsm/l higher than the osmolarity of the aqueous medium of step a) to apply an osmotic shock to the vesicles and to obtain buffer-filled vesicles and c) diluting a mixture of the aqueous medium and the basic or acidic buffer containing the buffer-filled vesicles by adding a neutralizing solution to obtain transmembrane pH-gradient vesicles suspended in a suspension buffer, which differs from the basic or acidic buffer in pH value.

14 Claims, 2 Drawing Sheets

(56) References Cited

U.S. PATENT DOCUMENTS

| | | | |
|---|---|---|---|
| 4,792,331 A | 12/1988 | Philippot et al. | |
| 5,049,392 A * | 9/1991 | Weiner | A61K 9/1278 |
| | | | 264/4.1 |
| 5,077,056 A | 12/1991 | Bally et al. | |
| 5,094,854 A | 3/1992 | Ogawa et al. | |
| 5,185,154 A | 2/1993 | Lasic et al. | |
| 5,230,899 A * | 7/1993 | Park | A61K 9/1277 |
| | | | 264/4.1 |
| 5,393,530 A | 2/1995 | Schneider et al. | |
| 5,622,713 A | 4/1997 | Mehlhorn | |
| 5,686,309 A * | 11/1997 | Frank | G01N 15/1031 |
| | | | 324/71.1 |
| 5,766,627 A | 6/1998 | Sankaram et al. | |
| 5,773,024 A | 6/1998 | Unger et al. | |
| 5,807,572 A | 9/1998 | Kim et al. | |
| 5,939,096 A | 8/1999 | Clerc et al. | |
| 6,045,824 A | 4/2000 | Kim et al. | |
| 6,106,858 A | 8/2000 | Ye et al. | |
| 6,149,937 A | 11/2000 | Camu et al. | |
| 6,162,462 A | 12/2000 | Bolotin et al. | |
| 6,306,432 B1 | 10/2001 | Shirley et al. | |
| 6,544,549 B1 | 4/2003 | Boni et al. | |
| 8,022,279 B2 | 9/2011 | Mayer et al. | |
| 8,951,450 B2 | 2/2015 | Shimizu et al. | |
| 9,226,984 B2 | 1/2016 | Petersen et al. | |
| 9,526,761 B2 | 12/2016 | Hellerbrand et al. | |
| 9,820,941 B2 * | 11/2017 | Madsen | A61P 35/00 |
| 2002/0136762 A1 | 9/2002 | See et al. | |
| 2003/0224039 A1 | 12/2003 | Boni et al. | |
| 2005/0031679 A1 | 2/2005 | Unger et al. | |
| 2005/0118249 A1 * | 6/2005 | Webb | A61K 9/1271 |
| | | | 424/450 |
| 2006/0034907 A1 * | 2/2006 | Nagaike | A61K 9/1277 |
| | | | 424/450 |
| 2006/0159736 A1 * | 7/2006 | Zalipsky | A61P 43/00 |
| | | | 424/450 |
| 2006/0239925 A1 * | 10/2006 | Wada | A61K 9/1277 |
| | | | 424/9.45 |
| 2007/0269502 A1 * | 11/2007 | Pliura | A61P 43/00 |
| | | | 424/450 |
| 2008/0107724 A1 * | 5/2008 | Szebeni | A61K 31/337 |
| | | | 424/450 |
| 2008/0274172 A1 | 11/2008 | Moscoso Del Prado et al. | |
| 2009/0017108 A1 | 1/2009 | Yuzhakov | |
| 2009/0092662 A1 * | 4/2009 | Huang | A61P 35/00 |
| | | | 424/450 |
| 2009/0092663 A1 * | 4/2009 | Ponzoni | A61K 31/00 |
| | | | 424/450 |
| 2009/0269396 A1 * | 10/2009 | Cipolla | A61K 9/0073 |
| | | | 424/450 |
| 2010/0021531 A1 * | 1/2010 | Yoshino | A61K 9/1278 |
| | | | 424/450 |
| 2010/0305500 A1 | 12/2010 | Lambert et al. | |
| 2011/0070292 A1 | 3/2011 | Javeri et al. | |
| 2011/0105995 A1 | 5/2011 | Zhu et al. | |
| 2011/0250264 A1 | 10/2011 | Schutt et al. | |
| 2012/0202882 A1 | 8/2012 | Banov et al. | |
| 2013/0230457 A1 * | 9/2013 | Reed | A61K 9/127 |
| | | | 424/1.21 |
| 2013/0259922 A1 | 10/2013 | Haas et al. | |
| 2013/0316980 A1 * | 11/2013 | Tchirikov | A61P 43/00 |
| | | | 514/78 |
| 2014/0205543 A1 | 7/2014 | Penate-Medina et al. | |
| 2015/0216802 A1 | 8/2015 | Leroux et al. | |
| 2015/0309057 A1 | 10/2015 | Gavin et al. | |

FOREIGN PATENT DOCUMENTS

| | | |
|---|---|---|
| CN | 103182333 A | 7/2013 |
| CN | 102716089 B | 12/2013 |
| EP | 0087993 A1 | 9/1983 |
| EP | 0331504 A1 | 9/1989 |
| EP | 0346472 A1 | 12/1989 |
| EP | 0461662 A1 | 12/1991 |
| EP | 0565361 A1 | 10/1993 |
| EP | 1547580 A1 | 6/2005 |
| EP | 2253308 A1 | 11/2010 |
| EP | 2394640 A1 | 12/2011 |
| EP | 2433619 A1 | 3/2012 |
| EP | 2474351 A1 | 7/2012 |
| JP | 564739 A | 3/1993 |
| JP | 69710 A | 1/1994 |
| JP | 2008136967 A | 6/2008 |
| JP | 2012158576 A | 8/2012 |
| WO | 8501440 A1 | 4/1985 |
| WO | 8801864 A1 | 3/1988 |
| WO | 8905636 A1 | 6/1989 |
| WO | 9003808 A1 | 4/1990 |
| WO | 9007920 A1 | 7/1990 |
| WO | 9014105 A1 | 11/1990 |
| WO | 9015595 A1 | 12/1990 |
| WO | 9608234 A1 | 3/1996 |
| WO | 9632930 A1 | 10/1996 |
| WO | 9734582 A1 | 9/1997 |
| WO | 9912522 A1 | 3/1999 |
| WO | 9912523 A1 | 3/1999 |
| WO | 9913865 A1 | 3/1999 |
| WO | 9916426 A2 | 4/1999 |
| WO | 0009089 A1 | 2/2000 |
| WO | 01/05372 * | 1/2001 |
| WO | 0105372 A2 | 1/2001 |
| WO | 0195914 A1 | 12/2001 |
| WO | 03039512 A1 | 5/2003 |
| WO | 03075890 A1 | 9/2003 |
| WO | 2005048986 A1 | 6/2005 |
| WO | 2005102359 A1 | 11/2005 |
| WO | 2008040556 A1 | 4/2008 |
| WO | 2009009115 A2 | 1/2009 |
| WO | 2009091531 A2 | 7/2009 |
| WO | 2011038073 A1 | 3/2011 |
| WO | 2012079582 A1 | 6/2012 |
| WO | 2012117587 A1 | 9/2012 |
| WO | 2014013043 A1 | 1/2014 |
| WO | 2014023421 A1 | 2/2014 |

OTHER PUBLICATIONS

Bertrand et al.; "Transmembrane pH-Gradient Liposomes To Treat Cardiovascular Drug Intoxication"; ACS Nano; 2010; pp. 7552-7558; vol. 4:12.

Forster et al.; "Liposome-supported peritoneal dialysis for detoxification of drugs and endogenous metabolites" Sci. Transl. Med.; 2014; pp. 1-9; vol. 6:258.

Forster et al.; "Treatment of calcium channel blocker-induced cardiovascular toxicity with drug scavenging liposomes"; Biomaterials; 2012; pp. 3578-3585; vol. 33.

Grit et al.; "Chemical stability of liposomes: implications for their physical stability"; Chemistry and Physics of Lipids; 1993; pp. 3-18; vol. 64.

Mayer et al.; "Uptake of antineoplastic agents into large unilamellar vesicles in response to a membrane potential" Biochimica et Biophysica Acta; 1985; pp. 294-302; vol. 816.

Mayer et al.; "Uptake of Dibucaine into Large Unilamellar Vesicles in Response to a Membrane Potential"; The Journal of Biological Chemistry; 1985; pp. 802-808; vol. 260:2.

Nichols et al.; "Catecholamine Uptake and Concentration By Liposomes Maintaining pH Gradients"; Biochimica et Biophysica Acta; 1976; pp. 269-271; vol. 455.

Stevens et al.; "Formulation Kit for Liposomal Doxorubicin Composed of Lyophilized Liposomes"; Anticancer Research; 2003; pp. 439-442; vol. 23.

Toh et al.; "Liposomes as sterile preparations and limitations of sterilisation techniques in liposomal manufacturing" Asian Journal of Pharmaceutical Sciences; 2013; pp. 88-95; vol. 8.

Zuidam et al.; "Sterilization of Liposomes by Heat Treatment"; Pharmaceutical Research; 1993; pp. 1591-1596; vol. 10:11.

Bertrand et al., "Transmembrane pH-Gradient Liposomes To Treat Cardiovascular Drug Intoxication", ACS Nano, 2010, vol. 4:12, pp. 7552-7558.

(56) References Cited

OTHER PUBLICATIONS

Yunbo, "Functional Food Processing Technology", China Quality and Standards Publishing & Media Co., Ltd., 2013, 23 pages. (Relevant for reasons stated in CN Office Action 201680025547.4 translation, p. 3).

Antimisiaris et al., "Liposomes and Drug Delivery," Pharmaceutical Sciences Encyclopedia: Drug Discovery, Development, and Manufacturing, 2010 1-91.

Chang et al. "Clinical-development-of-liposome-based-drugs," International Journal of Nanomedicine 2012:7 49-60.

Grit et al. "Chemical stability of liposomes: implications for their physical stability," Chemistry and Physics of Lipids, 64 (1993) 3-18.

Examination Report dated May 28, 2020, in Australian Patent Application No. 2016256979.

Examination Report dated Nov. 30, 2020, in Australian Patent Application No. 2016256979.

Office Action dated Jul. 16, 2020, in Mexican Patent Application No. MX/a/2017/014130.

Office Action dated Sep. 1, 2020 in Brazilian Patent Application No. 1120170235781.

\* cited by examiner

METHOD FOR PREPARING TRANSMEMBRANE PH-GRADIENT VESICLES

CROSS-REFERENCE TO RELATED APPLICATIONS

This application is the United States national phase of International Application No. PCT/EP2016/059912 filed May 3, 2016, and claims priority to European Patent Application No. 15166247.5 filed May 4, 2015, the disclosures of which are hereby incorporated in their entirety by reference.

BACKGROUND OF THE INVENTION

Field of the Invention

The instant invention relates to a method for preparing transmembrane pH-gradient vesicles.

Description of Related Art

The intravenous (Forster at al. Biomaterials 2012; 33:3578-3585) or intraperitoneal (Forster et al. Sci Transl Med 2014; 6: 258ra141) administration of vesicles (e.g. liposomes) with a remote loading capacity (e.g. transmembrane pH-gradient liposomes) have recently been described as an interesting approach for the treatment of drug overdose and intoxications to endogenous metabolites (e.g. hyperammonemia). These liposomes bear an internal compartment that contains acidic or basic buffering agents and which allows the sequestration of the toxic compounds in their ionized state via the existence of a pH-gradient between the inside compartment and outside environment.

According to prior art, transmembrane pH-gradient liposomes are generally prepared by hydration in an acidic or basic medium, followed by titration (Nichols and Deamer Biochimica et Biophysica Acta 1976; 455:269-271), medium exchange by gel filtration (Mayer et al. Biochimica et Biophysica Acta 1985; 816:294-302), or dialysis (Forster at al. Biomaterials 2012; 33:3578-3585), and then rapidly used to encapsulate drugs.

The sterilization of these vesicles is, according to prior art, performed on the final formulation containing the encapsulated compound. However, this approach is not adequate if a transmembrane pH-gradient is to be kept for prolonged period of times, as in the case of biodetoxifying agents, and/or if the liposomes are sterilized under high temperatures. Indeed, over time the transmembrane pH gradient decreases due to the diffusion of chemical species across the liposomal membrane and/or the degradation of the lipid components of the lipid bilayer (mainly the phospholipids). Moreover the chemical degradation of liposomal components (mainly the phospholipids) can be accelerated in basic or acidic media, especially if the sterilization process involves heat (e.g. autoclave).

A solution to this problem described by Stevens and Lee (Stevens and Lee Anticancer Res. 2003; 23:439-442) consists in preparing sterile freeze dried liposomes that are then suspended in an acidic or basic medium, followed by neutralization to generate the transmembrane pH-gradient. This approach involves a freeze drying step which generally implies the preparation of liposomes under aseptic conditions, a process which can be costly and difficult to control, especially when large volumes are to be freeze dried. This approach is therefore not ideal from an industrial viewpoint. Moreover, the fast resuspension of freeze dried liposomes in a reproducible manner can be problematic if large amounts of lipids are used, as in case of biodetoxification applications (e.g. peritoneal dialysis).

U.S. Pat. No. 5,393,530 A describes a method to remotely loading liposomal vesicles. Thereby, transmembrane loading is achieved by mixing a liposomal solution of low osmolarity (osmotic concentration) with the substance to be encapsulated. Then, the mixture is heated to a temperature above the membrane lipid transition temperature ($T_c$) of the lipids that make up the liposomal vesicle to achieve a membrane destabilization and to incorporate the substance into the inner part of the vesicles.

Bertrand et al. (ACS nano 2010; 4: 7552-7558) describes a method for forming transmembrane pH gradient liposomes in which an acidic buffer is encapsulated into liposomes in a first step. In a second step, an external buffer around the liposomes is exchanged so that a transmembrane pH gradient between the interior of the formed liposomes and the exterior is established.

SUMMARY OF THE INVENTION

It is an object of the instant invention to provide a manufacturing process by which stable transmembrane pH-gradient vesicles can be produced in a simple manner without the before-mentioned limitations of prior art. In particular, an industrial application of the manufacturing process shall be possible.

This object is achieved by a method for preparing transmembrane pH-gradient vesicles having features as described herein.

Such a method comprises the steps explained in the following. In a first step, vesicles made from at least one matrix substance are prepared in an aqueous medium having an osmolarity of not more than 200 mOsm/l. In an embodiment, the osmolarity of the aqueous medium is equal to or less than 150 mOsm/l, in particular equal to or less than 100 mOsm/l, in particular equal to or less than 75 mOsm/l, in particular equal to or less than 50 mOsm/l, in particular equal to or less than 25 mOsm/l, in particular equal to or less than 10 mOsm/l, in particular equal to or less than 5 mOsm/l, in particular equal to or less than 1 mOsm/l. In an embodiment, the osmolarity is in the range of 1 mOsm/l to 200 mOsm/l or in the range built up from any of the before-mentioned osmolarities (such as 10 mOsm/l to 150 mOsm/l etc.).

In a second step, the vesicles are mixed with a basic or acidic buffer having an osmolarity being at least 200 mOsm/l higher than the osmolarity of the aqueous medium of step a) to apply an osmotic shock to the vesicles and to obtain buffer-filled vesicles. In an embodiment, the osmolarity of the basic or acidic buffer is at least 220 mOsm/l higher than the osmolarity of the aqueous medium of step a), in particular at least 250 mOsm/l higher, in particular at least 300 mOsm/l higher, in particular at least 350 mOsm/l higher, in particular at least 400 mOsm/l higher, in particular at least 450 mOsm/l higher, in particular at least 500 mOsm/l higher, in particular at least 550 mOsm/l higher. In an embodiment, the osmolarity of the basic or acidic buffer is in a range of 200 mOsm/l to 550 mOsm/l higher than the osmolarity of the aqueous medium of step a) or in a range built up from any of the before-mentioned osmolarities (such as 220 mOsm/l to 500 mOsm/l etc.).

Thus, the basic or acidic buffer is a hyperosmotic buffer with respect to the aqueous medium used in the first step. In doing so, an osmotic shock is extemporaneously applied to the vesicles. This osmotic shock results in incorporating the acidic or basic buffer within the vesicles. Thus, the osmotic shock serves for a short-term destabilization of the vesicles in order to allow buffer incorporation into the vesicles. Buffer-filled vesicles result. In an embodiment, the hyperosmotic buffer can also contain electrolytes that are used to modulate the osmolarity or have a physiological function.

It should be noted that a sufficient amount of the basic or acidic buffer is to be added to the vesicles suspended in the aqueous medium since otherwise no osmotic shock will be achieved. A sufficient amount can be in dependence on the difference between the osmolarity of the aqueous medium and the osmolarity of the acidic or basic buffer a volume that corresponds to at least 0.1 times the volume of the aqueous medium used in the first step, in particular at least 0.3 times, in particular at least 0.5 times, in particular at least 0.8 times, in particular at least 1.5 times, in particular at least 2 times, in particular at least 2.5 times, in particular at least 3 times and in particular at least 5 times in particular. In an embodiment, the basic or acidic buffer can be added in a volume that equals the volume of the aqueous medium. In an embodiment, the volume of the basic or acidic buffer to be added can be 0.1 times to 5 times the volume of the aqueous vesical suspension or any other range that can be built up from the before-mentioned values (such as 0.3 times to 3 times, etc.).

In an embodiment, the pH value of the hyperosmotic buffer is in a range of pH 1 to pH 6.9, in particular pH 1.5 to pH 6.5, in particular pH 2.0 to pH 6.0, in particular pH 2.5 to pH 5.5, in particular pH 3.0 to pH 5.0, in particular pH 3.5 to pH 4.5, in particular pH 3.0 to pH 3.5.

In an embodiment, the pH value of the hyperosmotic buffer is in a range of pH 7.1 to pH 14, in particular pH 7.5 to pH 13.5, in particular pH 8.0 to pH 13.0, in particular pH 8.5 to pH 12.5, in particular pH 9.0 to pH 12.0, in particular pH 9.5 to pH 11.5, in particular pH 10.0 to pH 11.0, in particular pH 10.5 to pH 11.0.

In an embodiment, the hyperosmotic buffer can contain additional chemical agents such as a complexing agent or chelating agent.

In a third step, a mixture of the aqueous medium and the basic or acidic buffer containing the buffer-filled vesicles is diluted by adding a neutralizing aqueous solution. The mixture of basic or acidic buffer and neutralizing solution makes up a suspension buffer. Thus, after dilution, transmembrane pH-gradient vesicles suspended in the suspension buffer result. Thereby, the pH of the suspension buffer differs from the basic or acidic buffer contained in the buffer-filled vesicles The pH difference is in an embodiment at least 1 pH unit, in particular at least 1.5 pH units, in particular at least 2 pH units, in particular at least 2.5 pH units, in particular at least 3 pH units, in particular at least 3.5 pH units, in particular at least 4 pH units, in particular at least 4.5 pH unit, in particular at least 5 pH units, in particular at least 5.5 pH units, in particular at least 6 pH units, in particular at least 6.5 pH units, in particular at least 7 pH units.

In an embodiment, the pH value of the neutralizing solution is in a range of pH 7.1 to pH 14, in particular pH 7.5 to pH 13.5, in particular pH 8.0 to pH 13.0, in particular pH 8.5 to pH 12.5, in particular pH 9.0 to pH 12.0, in particular pH 9.5 to pH 11.5, in particular pH 10.0 to pH 11.0, in particular pH 10.5 to pH 11.0.

In an embodiment, the pH value of the neutralizing solution is in a range of pH 1 to pH 6.9, in particular pH 1.5 to pH 6.5, in particular pH 2.0 to pH 6.0, in particular pH 2.5 to pH 5.5, in particular pH 3.0 to pH 5.0, in particular pH 3.5 to pH 4.5, in particular pH 3.0 to pH 3.5.

Due to the differences of the suspension buffer and the basic or acidic buffer, a transmembrane pH-gradient between the inner part of the vesicles and the surrounding suspension buffer is achieved.

In an embodiment, the vesicles prepared in the first step are sterilized so as to obtain sterilized vesicles or a sterilized vesicles-containing liquid solution. Then, these sterilized vesicles are used when carrying out the second step of the manufacturing process explained above. In this second step, a sterilized basic or acidic buffer is used in an embodiment. In doing so, fully sterile buffer-filled vesicles or a fully sterile solution containing buffer-filled vesicles can be prepared. The sterilization can be carried out by, e.g., sterile filtration or autoclaving.

In another embodiment, the vesicles are stored for a first period of time prior to carrying out the step of mixing the vesicles (or the vesicles-containing solution) with the basic or acidic buffer. This storage can be accomplished in a very suited manner if the vesicles are sterilized after the first preparation step because then no or little degradation processes will occur in the sterilized vesicle suspension. The first period of time can be one day, a few days, one week, several weeks, one month or even several months. It should be noted that sterilized vesicles contained in an aqueous medium are stable entities. Since they do not yet contain any specific acidic or basic buffer like later on when using the vesicles, no buffer loss due to vesicle degradation or leakage of the vesicles has to be feared. This is also true if the vesicles, in an embodiment, contain low amounts of electrolytes molecules since an according osmolarity within the vesicles would then be in a range of between 1 mOsm/l to 200 mOsm/l. In addition, since the vesicles are kept in an aqueous medium during storage, no disadvantages like in the case of lyophilizing the vesicles occur.

Since the incorporation of the basic or acidic buffer is achieved by a strong osmotic shock, no vesicle destabilization via an enhanced temperature is necessary. In particular, it is not necessary to heat the vesicles onto a temperature that is above the transition temperature of the matrix substance used for preparing the vesicles. It was rather surprising to find out that the step of incorporating buffer into the vesicles does not have to be performed above the membrane lipid phase transition temperature, if lipids are used as matrix substance.

Therefore, in an embodiment, the second step of the method is carried out at a temperature that is below a phase transition temperature of the matrix substance. Such phase transition temperature can be the membrane lipid transition temperature if a lipid is used as matrix substance.

In an embodiment, the second step of the method is carried out at a temperature of 35° C. or less, in particular of 30° C. or less, in particular of 25° C. or less, in particular of 20° C. or less, in particular of 15° C. or less, in particular of 10° C. or less. To give an example, a suited temperature range for carrying out the second step is 15 to 35° C. In addition, further temperature ranges using the before-mentioned temperatures can be built up as desired and needed (e.g. 10 to 30° C. etc.). In another embodiment, the whole manufacturing method is carried out at the before-mentioned temperatures or temperature ranges (in some embodiments excluding the sterilization process, namely, in particular if the sterilization process is carried out as autoclaving).

In an embodiment, the neutralizing solution has an osmolarity of between 250 mOsm/l and 550 mOsm/l, in particular of between 270 and 520 mOsm/l, in particular of between 290 and 500 mOsm/l, in particular of between 300 and 480 mOsm/l, in particular of between 320 and 450 mOsm/l, in particular of between 330 and 420 mOsm/l, in particular of between 350 and 400 mOsm/l.

In an embodiment, the neutralizing solution has an osmolarity which is less than 200 mOsm/l higher or lower than the osmolarity of the mixture containing the buffer-containing vesicles (i.e., the buffer-containing vesicles solution), in particular less than 150 mOsm/l higher or lower, in particular less than 100 mOsm/l higher or lower, in particular less than 50 mOsm/l higher or lower, in particular less than 20 mOsm/l higher or lower, in particular less than 10 mOsm/l higher or lower. In an embodiment, the difference in osmolarity between the neutralizing solution and the mixture containing the buffer-containing vesicles is between 1 mOsm/to 200 mOsm/l, in particular between 10 mOsm/to 150 mOsm/l, in particular between 20 mOsm/to 100 mOsm/l, in particular between 30 mOsm/to 80 mOsm/l, in particular between 40 mOsm/to 60 mOsm/l.

In an embodiment, the osmolarity of the hyperosmotic buffer is equal to or higher than 250 mOsm/l, in particular equal to or higher than 300 mOsm/l, in particular equal to or higher than 350 mOsm/l, in particular equal to or higher than 400 mOsm/l, in particular equal to or higher than 450 mOsm/l, in particular equal to or higher than 500 mOsm/l, in particular equal to or higher than 550 mOsm/l, in particular equal to or higher than 600 mOsm/l, in particular equal to or higher than 700 mOsm/l, in particular equal to or higher than 800 mOsm/l, in particular equal to or higher than 900 mOsm/l, in particular equal to or higher than 1000 mOsm/l, in particular equal to or higher than 1100 mOsm/l, in particular equal to or higher than 1200 mOsm/l, in particular equal to or higher than 1300 mOsm/l, in particular equal to or higher than 1400 mOsm/l, in particular equal to or higher than 1500 mOsm/l, in particular equal to or higher than 1600 mOsm/l, in particular equal to or higher than 1700 mOsm/l, in particular equal to or higher than 1800 mOsm/l, in particular equal to or higher than 1900 mOsm/l, in particular equal to or higher than 2000 mOsm/l. In an embodiment, the osmolarity is in the range of 250 mOsm/l to 2000 mOsm/l or in the range built up from any of the before-mentioned osmolarities (such as 300 mOsm/l to 1400 mOsm/l etc.).

In an embodiment, the mixture of the aqueous medium and the basic or acidic buffer in which the buffer-filled vesicles are suspended at the end of step b) has an osmolarity of at least 200 mOsm/l, in particular of at least 220 mOsm/l, in particular of at least 250 mOsm/l, in particular of at least 300 mOsm/l, in particular of at least 350 mOsm/l, in particular of at least 400 mOsm/l, in particular of at least 450 mOsm/l, in particular of at least 500 mOsm/l, in particular of at least 550 mOsm/l. In an embodiment, the osmolarity is in the range of 200 mOsm/l to 550 mOsm/l or in the range built up from any of the before-mentioned osmolarities (such as 220 mOsm/l to 500 mOsm/l etc.).

In an embodiment, the neutralizing solution has a composition that serves for not disrupting the buffer filled vesicles so as to not destabilize these vesicles. It may contain neutralizing species (basic or acidic, such as weak bases or weak acids) but also chemical agents used to adjust the osmolarity and/or provide a physiological function. It was found that the addition of glycerol and tris((hydroxymethyl) aminomethane) (TRIS) to the neutralizing solution is particularly interesting as it allows the inclusion of higher concentrations of calcium salts. Calcium salts can be added in the preparation process to counteract the anticoagulant effects of some weak acids (e.g. citric acid). This is in particular importance is the vesicles are to be used in in vivo applications. Sodium hydroxide, sodium salts (like NaCl), magnesium salts, lactate salts, glycerol, icodextrin, glucose, sorbitol, fructose, amino acids or xylitol can also be used as ingredients of the neutralizing solution.

In an embodiment, the pH value of the suspension buffer containing the transmembrane pH-gradient vesicles is in the range of 5.5 to 8.5, in particular of 6.0 to 8.0, in particular of 6.5 to 7.7, in particular of 6.8 to 7.5, in particular of 7.0 to 7.4. Thus, the suspension buffer might have a physiological pH value.

In an embodiment, the aqueous medium is neither an acid nor a base but has a pH value of around 7, e.g. in the range of 6.0 to 7.5, in particular of 6.1 to 7.4, in particular of 6.2 to 7.3, in particular of 6.3 to 7.2, in particular of 6.4 to 7.1, in particular of 6.5 to 7.3, in particular of 6.6 to 7.3, in particular of 6.7 to 7.3, in particular of 6.8 to 7.3, in particular of 6.9 to 7.1, in particular of 6.95 to 7.01, in particular a pH value of 7.0. Thus, the aqueous medium can also referred to as neutral aqueous medium.

In an embodiment, the aqueous medium is chosen from the group consisting of water, aqueous solutions of organic salts, aqueous solutions of inorganic salts, aqueous solutions of organic substances, and combinations thereof.

In an embodiment, the aqueous medium is chosen from the group consisting of aqueous solutions of organic salts having a pH value of around 7, aqueous solutions of inorganic salts having a pH value of around 7, aqueous solutions of organic substances having a pH value of around 7, water and combinations thereof.

The water can, e.g., be distilled water, deionized water, ultrapure water or any other kind of purified water. When using organic or inorganic salts or other organic compounds, these salts or compounds are present in the aqueous medium, in an embodiment, in a low concentration so as to keep a difference in osmolarity between the aqueous medium and the hyperosmotic buffer provoking the osmotic shock which difference is large enough to induce the diffusion of the acidic or basic hyperosmotic buffer into the vesicle internal compartment.

The aqueous medium is a medium that resembles water (in particular with respect to pH) but that might contain a low concentration of salts or compounds, e.g. for buffering the pH value in a neutral range. In an embodiment, the osmolarity of the aqueous medium is in a range between 0 mOsm/l and 49 mOsm/l, in particular between 5 mOsm/l and 45 mOsm/l, in particular between 10 mOsm/l and 40 mOsm/l, in particular between 15 mOsm/l and 35 mOsm/l, in particular between 20 mOsm/l and 30 mOsm/l, in particular between 25 mOsm/l and 28 mOsm/l.

In an embodiment, the matrix substance is chosen from the group consisting of amphiphilic lipids and amphiphilic block copolymers. If amphiphilic lipids are used, liposomes are formed as vesicles. Suited liposomes are multilamellar vesicles (MLV), small unilamellar vesicles (SUV) and large unilamellar vesicles (LUV).

If amphiphilic block copolymers are used, polymersomes are formed as vesicles. Suited amphiphilic block copolymers are linear diblock or triblock copolymers. The block copolymers can have one block that is hydrophobic and one or two other blocks that are hydrophilic. Comb copolymers are also possible, wherein a backbone block of such a comb copolymer can be hydrophilic and the comb branches can be hydrophobic. Dendronized block copolymers are also possible, wherein a dendrimer portion of these copolymers can be hydrophilic. In all cases, hydrophilic blocks can be made up from poly(ethylene glycol) (PEG/PEO) or poly(2-ethyloxazoline). In addition, hydrophobic blocks can be made up in all cases from poly(dimethylsiloxane) (PDMS), poly(caprolactone) (PCL), poly(lactide) (PLA) or poly(methyl methacrylate) (PMMA).

In an embodiment, the matrix substance is at least one amphiphilic lipid chosen from the group consisting of dipalmitoylphosphatidylcholine (DPPC), 1,2-distearoyl-sn-glycero-3-phosphoethanol-amine-N-[methoxy(PEG)-2000] (DSPE-PEG), cholesterol, 1-palmitoyl-2-oleoyl-sn-glycero-3-phosphocholine (POPC), and combinations thereof.

In an aspect, the instantly claimed invention also relates to transmembrane pH-gradient vesicles that can be obtained by a method according to the above-given explanations. These transmembrane pH-gradient vesicles differ in their stability from vesicles known from prior art. This is due to structural differences that result from the specific manufacturing process outlined above. Thus, the vesicles made according to the process explained above are not yet known from prior art.

In an aspect, the use of these transmembrane pH-gradient vesicles as detoxifying agent in vitro or in vivo (in humans or animals, in particular mammals or rodents) is claimed. They can be used to extract and bind unwanted substances such as overdosed drugs and poisons (or their metabolites) or high amounts of endogenous metabolites that can result in intoxications. Examples of substances that can be taken up by the transmembrane pH-gradient vesicles are ammonia and propionic acid. Removing ammonia and propionic acid from a solution (either in vivo or in vitro) results in a detoxification of such a solution from ammonia and/or propionic acid.

All embodiments disclosed herein can be combined in any desired way. Embodiments of the described method can be transferred to the described vesicles and the described uses, and vice versa.

BRIEF DESCRIPTION OF THE DRAWINGS

Further aspects and details of the instant invention will be explained with respect to the Figures and to the following examples.

DETAILED DESCRIPTION OF THE INVENTION

Example 1

Liposomes' formulation. Liposomes composed of dipalmitoylphosphatidylcholine (DPPC, Lipoid), cholesterol (Sigma-Aldrich) and 1,2-distearoyl-sn-glycero-3-phosphoethanol-amine-N-[methoxy(PEG)-2000] (DSPE-PEG, Lipoid) at 85:14:1 mol % were prepared by the film hydration method. 1685 mg of DPPC, 146 mg of cholesterol and 75 mg of DSPE-PEG were co-dissolved in 10 mL of dichloromethane:methanol 95:5% v/v. The organic solvent was subsequently removed by rotary evaporation and the lipid film was kept under vacuum overnight. The dried film was hydrated with 27 mL of ultra-pure water (lipids concentration=100 mM) while heating and slowly mixing 45 min at 56° C. and finally sterilized in sealed bottles by autoclaving 20 min at 121° C.

Stability. The liposomes were subjected to steam sterilization in an autoclave to assess their degradation by the applied heat. It is known that liposomes filled with an acid or a base are subject to acidic or basic hydrolysis, respectively. The instantly formed liposomes did not degrade at all due to the steam sterilization.

Figure 1:
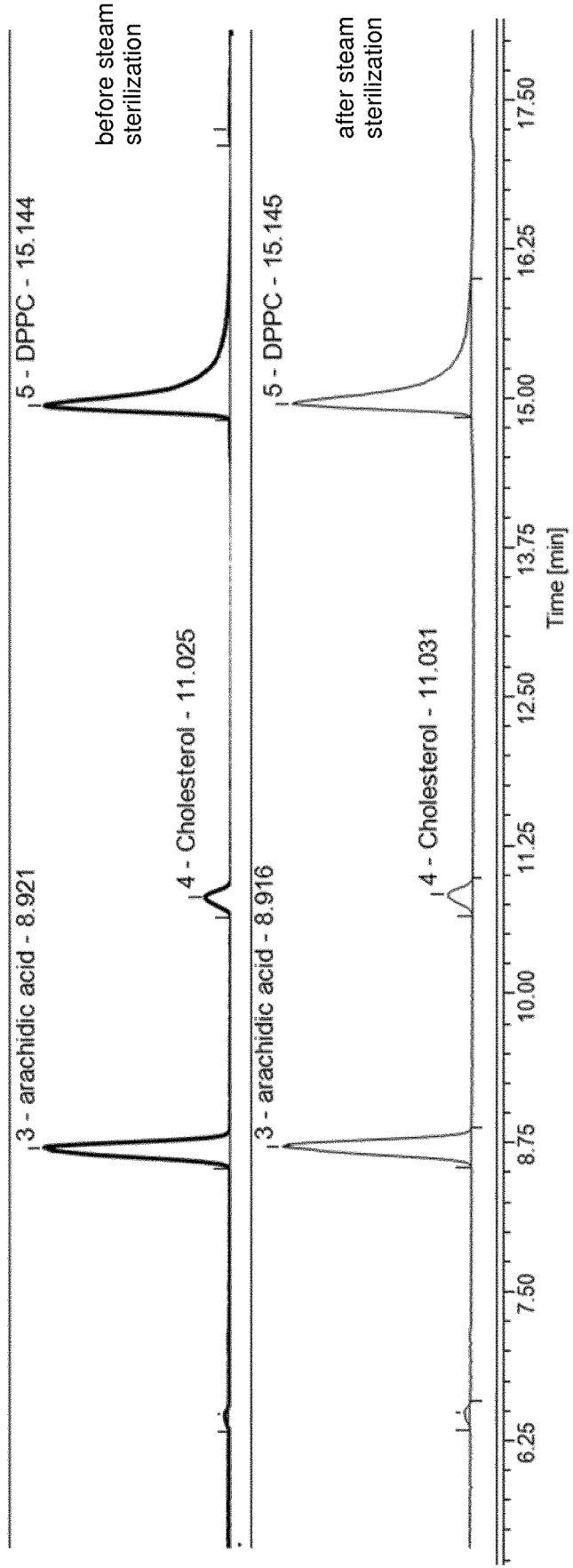
FIG. 1 shows HPLC-Charge aerosol detector (CAD) traces of an embodiment of a liposomal aqueous suspension before steam sterilization (upper panel) and after steam sterilization (lower panel)

As shown in FIG. 1, HPLC-Charge aerosol detector (CAD) traces of liposomal aqueous suspension before steam sterilization (upper panel of FIG. 1) and after steam sterilization (lower panel of FIG. 1) overlap.

Figure 2:
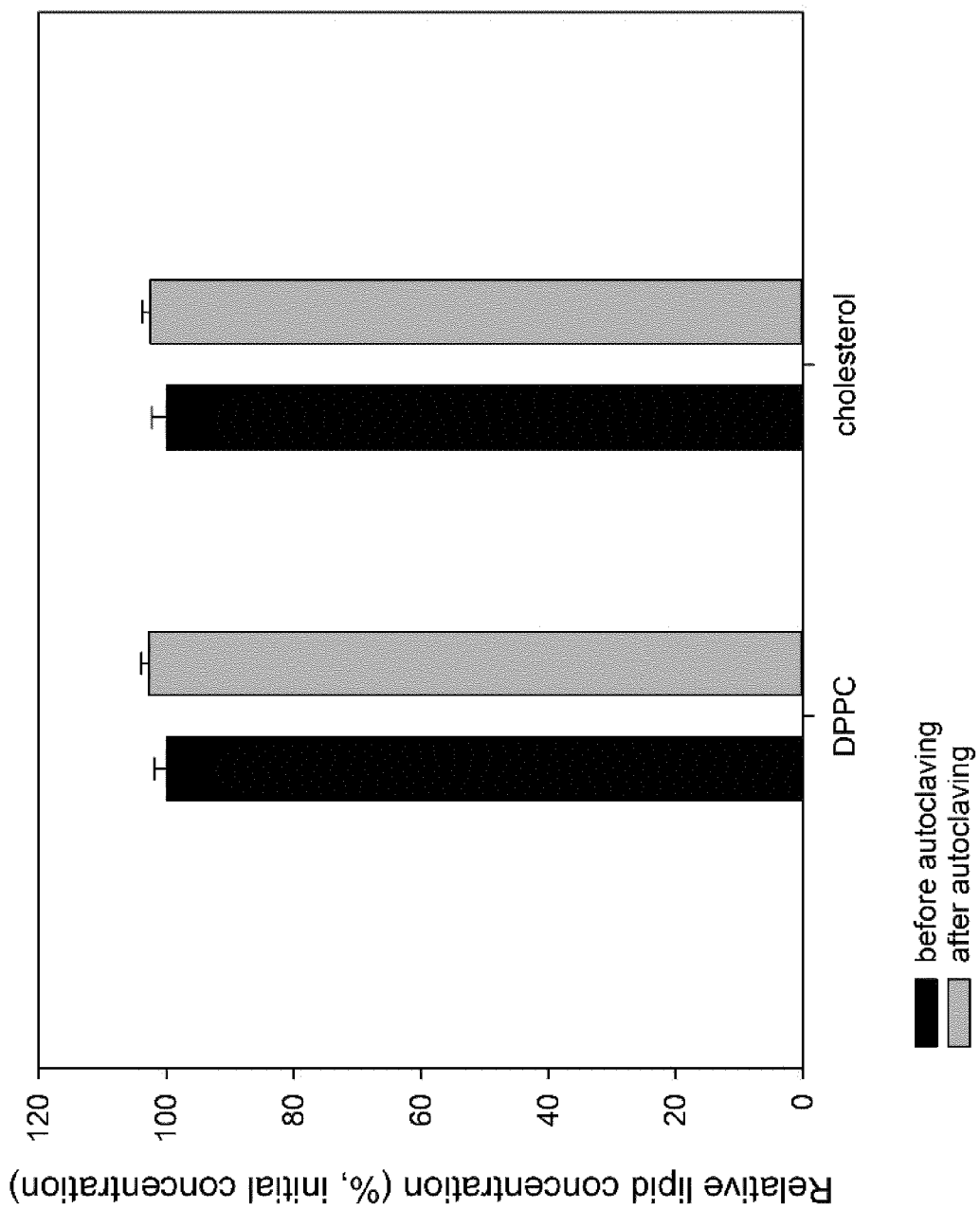
FIG. 2 shows the relative lipid concentration of an embodiment of liposomes before and after steam sterilization.

These results are confirmed by an assessment of the relative lipid concentration of the liposomes. As can be seen in FIG. 2, the relative lipid concentration remained stable after steam sterilization compared to the relative lipid concentration before steam sterilization. If hydrolysis would have been observed, the lipid concentration would have decreased.

Osmotic shock. The as-obtained liposomes were incubated 30 min with 27 mL of citrate buffer 400 mM (pH 2, 700 mOsm/l) containing citric acid (citric acid monohydrate) 290 mM, calcium citrate (calcium citrate tribasic tetrahydrate) 55 mM and HCl 80 mM. The incubation was performed under orbital shaking, at room temperature.

Generation of gradient. The transmembrane pH-gradient was generated by neutralizing the external acid medium with 106 mL of neutralization solution (pH=10.6, 410 mOsm/l) made of Tris (tris(hydroxymethyl)aminomethane, Panreac Applichem) 280 mM and calcium chloride (calcium chloride dehydrate, Merck Millipore) 50 mM. The resulting liposomes formulation 16.9 mM, pH 7.4, 312 mOsm/l was used for in vitro ammonia uptake studies.

In vitro ammonia uptake. Side-by-side diffusion cells (PermGear) maintained at 37° C. were used to monitor the ammonia uptake in HEPES-buffered saline (20 mM, 300 mOsm/l). The liposomes were physically isolated in one side of the dual-chamber system by a polycarbonate membrane (pore size=100 nm, Steriltech). The liposomes and the ammonia concentrations within the diffusion cells were 4.2 and 1.5 mM, respectively. At the allotted time, aliquots of 50 µL were sampled from the liposomes-free compartment and the ammonia concentration was assessed by enzymatic assay (Ammonia enzymatic kit, Sigma Aldrich). The ammonia uptake was quantified by means of the following equations (Eq. 1 and 2):

$$\text{Uptake} = \frac{\text{mmol Encapsulated Ammonia}}{\text{mmol Lipids}} = \frac{\text{mmol Total Ammonia} - \text{mmol Free Ammonia}}{\text{mmol Lipids}} \quad [\text{Eq. 1}]$$

$$\text{Uptake (\%)} = \frac{\text{Uptake}}{\text{Maximal uptake}} \times 100 = \frac{\text{Uptake}}{\text{mmol Total Ammonia/mmol lipids}} \times 100 \quad [\text{Eq. 2}]$$

After 5 h of incubation the ammonia uptake, calculated as per Eq. 2, was 82±5%.

Example 2

Liposomes' formulation. Liposomes composed of DPPC, cholesterol and DSPE-PEG were prepared and sterilized as above described (Example 1).

Osmotic shock. The as-obtained liposomes were incubated 30 min with 13.5 mL of citrate buffer 600 mM (pH 2, 1040 mOsm/l) containing citric acid 490 mM, calcium citrate 55 mM, sodium chloride (Fischer Scientific) 125 mM and HCl 135 mM. The incubation was performed under orbital shaking, at room temperature.

Generation of gradient. The transmembrane pH-gradient was generated by diluting the liposomes with 119.5 mL of neutralization solution (pH 10.6, 440 mOsm/l) made of Tris 160 mM, calcium chloride 35 mM and sodium chloride 100 mM. The final liposomes formulation 16.9 mM, pH 7.5 was used for in vitro ammonia uptake studies.

In vitro ammonia uptake. The in vitro ammonia uptake was studied by means of side-by-side diffusion cells as above described (Example 1). After 5 h of incubation, the average ammonia uptake within the liposomes was 92±8%.

Example 3

Liposomes' formulation. Liposomes composed of DPPC, cholesterol and DSPE-PEG were prepared and sterilized as above described (Example 1).

Osmotic shock. The osmotic shock was performed by incubating the liposomes as described in Example 2.

Generation of gradient. The transmembrane pH-gradient was generated by diluting the liposomes with 119.5 mL of neutralization solution (pH=12.7, 480 mOsm/l) made of sodium hydroxide 155 mM, glycerol, 210 mM, calcium chloride 20 mM and Tris 20 mM. The resulting liposomes formulation 16.9 mM was pH 6 and 341 mOsm/l.

In vitro ammonia uptake. The in vitro ammonia uptake was studied by means of side-by-side diffusion cells as above described (Example 1). The average ammonia uptake after 5 h of incubation was 96±3%.

Example 4

Liposomes' formulation. Liposomes composed of 1-palmitoyl-2-oleoyl-sn-glycero-3-phosphocholine (POPC, Lipoid), cholesterol and DSPE-PEG at 54:45:1 mol % were prepared by the film hydration method. 1108 mg of POPC, 469 mg of cholesterol and 75 mg of DSPE-PEG were co-dissolved in 10 mL of dichloromethane:methanol 95:5% v/v. The organic solvent was subsequently removed by rotary evaporation and the lipid film was kept under vacuum overnight. The dried film was hydrated with 27 mL of ultra-pure water (lipids concentration=100 mM) while heating and slowly mixing for 30 min at 56° C. and finally sterilized in sealed bottles by autoclaving 20 min at 121° C.

Osmotic shock. The osmotic shock was performed by incubating the liposomes as described in Example 2.

Generation of gradient. The transmembrane pH-gradient was generated by diluting the liposomes with 119.5 mL of neutralization solution (pH=12.7, 480 mOsm/l) made of sodium hydroxide 150 mM, glycerol 220 mM, calcium chloride 10 mM and Tris 20 mM. The resulting liposomes formulation 16.9 mM was pH 7.4 and 350 mOsm/l.

In vitro ammonia uptake. The in vitro ammonia uptake was studied by means of side-by-side diffusion cells as above described (Example 1). After 5 h of incubation, the ammonia uptake was 53.5±8.7%.

Example 5

Liposomes' formulation. Liposomes composed of DPPC, cholesterol and DSPE-PEG were prepared and sterilized as above described (Example 1).

Osmotic shock. The liposomes were incubated with 13.5 mL of calcium acetate buffer (pH 10, 1050 mOsm/l) 30 min, under orbital shaking, at room temperature. The buffer contained calcium acetate 350 mM, sodium hydroxide 0.75 mM.

Generation of gradient. The liposomes were diluted with 33 mL of a solution (pH=6.7, 380 mOsm/l) containing glycerol 230 mM, sodium chloride 50 mM, Tris 20 mM and acetic acid 20 mM. The resulting liposomes formulation 30 mM, pH 7, 335 mOsm/l was used for in vitro uptake studies of propionc acid.

In vitro uptake of propionic acid. Side-by-side diffusion cells maintained at 37° C. were used to monitor the in vitro uptake of a propionic acid solution labeled with 1% [1-14C] propionic acid (50 mCi/mmol, BIOTREND Chemikalien). The liposomes were physically isolated in one side of the dual-chamber system by a polycarbonate membrane (pore size=100 nm). The liposomes and the proprionic acid concentrations within the diffusion cells were 4.2 and 1.5 mM, respectively, after dilution with HEPES-buffered saline (20 mM, 300 mOsm/l). At the allotted time intervals (6-30 min, 1-2-3-4-5 h), aliquots of 50 µL were sampled from the liposomes-free compartment, mixed with 3 mL of Ultima Gold cocktail (Perking Elmer) and the radioactivity (beta decay) in each sample was assessed by scintillation counting (LS 6500 Scintillation Counter, Beckman). The metabolite concentration was determined by comparing the decay with a calibration curve, whose linearity was verified within the range of 31 µM to 2 mM. The propionic acid (PA) uptake was quantified by means of the following equations (Eq. 3 and 4):

$$\text{Uptake} = \frac{\text{mmol Encapsulated } PA}{\text{mmol Lipids}} = \frac{\text{mmol Total } PA - \text{mmol Free } PA}{\text{mmol Lipids}} \quad [\text{Eq. 3}]$$

$$\text{Uptake } (\%) = \frac{\text{Uptake}}{\text{Maximal uptake}} \times 100 = \frac{\text{Uptake}}{\text{mmol Total } PA/\text{mmol lipids}} \times 100 \quad [\text{Eq. 4}]$$

After 5 h of incubation, the propionic acid uptake, calculated as per Eq. 4 was 25±3%.

Example 6

Liposomes' formulation. Liposomes composed of DPPC, cholesterol and DSPE-PEG were prepared and sterilized as above described (Example 1).

Osmotic shock. The as-obtained liposomes were incubated 30 min with 13.5 mL of citrate buffer 600 mM (pH 2, 1050 mOsm/l) containing citric acid 490 mM, calcium citrate 15 mM, sodium citrate (Sigma Aldrich) 74 mM, Magnesium citrate (Applichem Panreac) 6 mM, sodium chloride 35 mM and HCl 178 mM. The incubation was performed under orbital shaking, at room temperature.

Generation of gradient. The transmembrane pH-gradient was generated by diluting the liposomes with 279.5 mL of neutralization solution (pH=12.6, 360 mOsm/l) made of sodium hydroxide 43 mM, xylitol (ABCR Gmbh) 260 mM, calcium chloride 1 mM, Tris 20 mM, sodium chloride 15 mM. The resulting liposomes formulation 8.4 mM, pH 6.4, 350 mOsm/l was used for in vivo ammonia uptake studies.

In vivo ammonia uptake. Six adult male Sprague-Dawley rats (weighing about 300 g; Charles River Laboratories) were allowed 5 days to acclimate to the surroundings; they had access to food and water ad libitum, and they followed a 12-h light/dark cycle. On the day of the experiment, the freshly prepared dialysis solution 16.7 mM was prewarmed to 37° C. and slowly infused (60 mL/kg) in the peritoneal cavity of rats kept under isoflurane anesthesia (2.5% in 0.8 mL/min oxygen flow). The instillation was performed with a 20-gauge hypodermic needle. At the allotted time, the rats were briefly anesthetized (using isoflurane inhalation, under similar conditions), and about 400 µL of dialysate was withdrawn through a sterile abdominal puncture with a 22-gauge perforated silicone catheter (Venflon; Becton Dickinson). The aliquots were immediately frozen in liquid nitrogen and kept at 80° C. for additional ammonia content determination by enzymatic assay (Enzymatic Ammonia Assay, Sigma Aldrich). Before running the assay, 100 µL of each sample were diluted with 50 µL of Triton-X-100 (3%) and sonicated in an ultrasonic bath for 5 min. The animal experiment was performed in accordance with procedures and protocols approved by the cantonal veterinary authorities (Kantonales Veterinäramt Zürich). At the end of the experiment, the animals were euthanized either by carbon dioxide asphyxia followed by a thoracotomy. The average ammonia concentration found in the dialysate samples after 4 h of treatment was 1.25±0.2 mM.

The invention claimed is:

1. A method for preparing transmembrane pH-gradient vesicles, comprising the steps of:
   a) preparing vesicles made from at least one matrix substance in an aqueous medium having an osmolarity of not more than 200 mOsm/l and a pH in the range of 6.0 to 7.5, wherein the matrix substance is chosen from the group consisting of amphiphilic lipids and amphiphilic block copolymers, sterilizing the vesicles, and, optionally, storing the sterilized vesicles,
   b) mixing the sterilized vesicles with a sterile basic or acidic buffer having an osmolarity being at least 200 mOsm/l higher than the osmolarity of the aqueous medium of step a) to apply an osmotic shock to the vesicles and to obtain buffer-filled vesicles, wherein the basic or acidic buffer is added in an amount sufficient to cause temporary destabilization of the vesicles in step b), and
   c) diluting a mixture of the aqueous medium and the basic or acidic buffer containing the buffer-filled vesicles by adding a sterile neutralizing solution to obtain sterile transmembrane pH-gradient vesicles suspended in a sterile suspension buffer, wherein the suspension buffer differs from the basic or acidic buffer in pH value, and wherein the neutralizing solution does not destabilize the vesicles in step c).

2. The method according to claim 1, wherein the vesicles are stored for a first period of time prior to carrying out step b).

3. The method according to claim 1, wherein step b) is carried out at a temperature that is below a phase transition temperature of the matrix substance.

4. The method according to claim 1, wherein step b) is carried out at a temperature of not more than 35° C.

5. The method according to claim 1, wherein the osmolarity of the basic or acidic buffer is at least 250 mOsm/l.

6. The method according to claim 1, wherein the mixture of the aqueous medium and the basic or acidic buffer in which the buffer-filled vesicles are suspended at the end of step b) has an osmolarity of at least 200 mOsm/l.

7. The method according to claim 1, wherein the neutralizing solution has an osmolarity of between 250 mOsm/l and 550 mOsm/l.

8. The method according to claim 1, wherein the neutralizing solution of step c) further comprises at least one substance chosen from the group consisting of glycerol, xylitol, TRIS, glucose, magnesium salts, sodium hydroxide, sodium salts and calcium salts.

9. The method according to claim 1, wherein the pH value of the suspension buffer containing the transmembrane pH-gradient vesicles is in a range of 5.5 to 8.5.

10. The method according to claim 1, wherein the aqueous medium is chosen from the group consisting of water, aqueous solutions of organic salts, aqueous solutions of inorganic salts, aqueous solutions of organic substances, and combinations thereof.

11. The method according to claim 1, wherein the matrix substance is chosen from the group consisting of dipalmitoylphosphatidylcholine, 1,2-distearoyl-sn-glycero-3-phosphoethanol-amine-N-[methoxy(PEG)-2000], cholesterol and 1-palmitoyl-2-oleoyl-sn-glycero-3-phosphocholine, and combinations thereof.

12. The method according to claim 1, wherein the vesicles prepared in step a) are sterilized by autoclaving.

13. The method according to claim 1, wherein the aqueous medium of step a) has an osmolarity that is equal to or less than 50 mOsm/L.

14. A method for preparing sterile transmembrane pH-gradient vesicles, comprising the steps of:
   a) mixing (i) a sterilized aqueous medium comprising sterilized vesicles filled with the aqueous medium, the vesicles being made from at least one matrix substance chosen from amphiphilic lipids, the aqueous medium having an osmolarity of not more than 200 mOsm/l and a pH in the range of 6.0 to 7.5, with (ii) a sterile basic buffer having a pH of at least 8.5 or a sterile acidic buffer having a pH of 5.5 or less, the sterile basic or acidic buffer having an osmolarity at least 400 mOsm/l higher than the aqueous medium, to apply an osmotic shock to the vesicles and to obtain basic or acidic buffer-filled vesicles, wherein the basic or acidic buffer is in an amount sufficient to cause temporary destabilization of the vesicles in step a); and
   b) diluting the mixture of step a) by adding a sterile neutralizing solution to obtain sterile transmembrane pH-gradient vesicles suspended in a sterile suspension buffer, wherein the suspension buffer differs from the basic or acidic buffer of step a) in pH value, and wherein the neutralizing solution does not destabilize the vesicles in step b).

* * * * *